United States Patent
Liu et al.

(10) Patent No.: US 10,825,643 B2
(45) Date of Patent: Nov. 3, 2020

(54) ACCELERATOR SYSTEM FOR MINERAL COMPONENT ANALYSIS, SYSTEM AND METHOD FOR MINERAL COMPONENT ANALYSIS

(71) Applicant: Nuctech Company Limited, Beijing (CN)

(72) Inventors: Yaohong Liu, Beijing (CN); Liang Zhang, Beijing (CN); Xiaotong Zhang, Beijing (CN); Feng Gao, Beijing (CN)

(73) Assignee: NUCTECH COMPANY LIMITED, Beijing (CN)

(*) Notice: Subject to any disclaimer, the term of this patent is extended or adjusted under 35 U.S.C. 154(b) by 0 days.

(21) Appl. No.: 16/231,672

(22) Filed: Dec. 24, 2018

(65) Prior Publication Data

US 2019/0198285 A1 Jun. 27, 2019

(30) Foreign Application Priority Data

Dec. 26, 2017 (CN) .......................... 2017 1 1435413

(51) Int. Cl.
*H01J 37/09* (2006.01)
*H01J 37/32* (2006.01)
(Continued)

(52) U.S. Cl.
CPC .............. *H01J 37/09* (2013.01); *G01N 33/20* (2013.01); *G01N 33/24* (2013.01); *H01J 37/065* (2013.01);
(Continued)

(58) Field of Classification Search
USPC .......................... 250/306, 307, 505.1, 492.2
See application file for complete search history.

(56) References Cited

U.S. PATENT DOCUMENTS

| | | | | | |
|---|---|---|---|---|---|
| 5,326,970 | A | * | 7/1994 | Bayless | .................... G01V 5/08 250/262 |
| 5,401,973 | A | * | 3/1995 | McKeown | ........... H05H 1/0006 250/396 R |

(Continued)

FOREIGN PATENT DOCUMENTS

| | | |
|---|---|---|
| CA | 2 932 676 A1 | 6/2015 |
| CN | 101349660 A | 1/2009 |

(Continued)

OTHER PUBLICATIONS

Canadian Examination Search Report dated Jun. 14, 2019 received in Canadian Application No. 3,028,509.
(Continued)

*Primary Examiner* — Kiet T Nguyen
(74) *Attorney, Agent, or Firm* — Scully Scott Murphy & Presser (57) ABSTRACT

The present application discloses an accelerator system for mineral component analysis and system and method for mineral component analysis. The accelerator system includes an electron gun for generating an electron beam; an accelerating tube for accelerating an electron beam emitted by the electron gun to a predetermined energy; a composite target for generating a radioactive ray on the composite target after receiving bombardment of the electron beam; and a shielding mechanism for shielding the radioactive ray.

15 Claims, 10 Drawing Sheets

(51) Int. Cl.
*H01J 37/065* (2006.01)
*G01N 33/20* (2019.01)
*G01N 33/24* (2006.01)

(52) U.S. Cl.
CPC ... *H01J 37/32229* (2013.01); *H01J 2237/026* (2013.01); *H01J 2237/0473* (2013.01); *H01J 2237/2487* (2013.01)

(56) References Cited

U.S. PATENT DOCUMENTS

| | | | |
|---|---|---|---|
| 5,428,658 | A | 6/1995 | Oettinger et al. |
| 6,002,734 | A | 12/1999 | Steinman |
| 8,455,820 | B2 | 6/2013 | Agemura et al. |

FOREIGN PATENT DOCUMENTS

| | | | |
|---|---|---|---|
| CN | 101788508 | A | 7/2010 |
| CN | 103226111 | A | 7/2013 |
| CN | 104717821 | A | 6/2015 |
| CN | 104865283 | A | 8/2015 |
| CN | 105879246 | A | 8/2016 |
| CN | 106132060 | A | 11/2016 |
| CN | 106879156 | A | 6/2017 |
| CN | 107884425 | A | 4/2018 |
| CN | 107979911 | A | 5/2018 |
| CN | 207911115 | U | 9/2018 |

OTHER PUBLICATIONS

Examination report No. 2 dated Jun. 23, 2020 received in Australian Patent Application No. AU 2018286570.

Tickner, J. et al., "Measurement of Gold and Other Metals in Electronic and Automotive Waste Using Gamma Activation Analysis", Journal of Sustainable Metallurgy, Mar. 17, 2016, pp. 296-303.

Demsky, M. et al., "Facility for Gamma Activation Analysis with 8 MeV, 10 kW Linear Accelerator", Low energy electron beams for industrial and environmental applications, EuCARD-2 Workshop with Industry, Dec. 8-9, 2016, pp. 1-31.

Office Action dated Jul. 7, 2020 received in Canadian Patent Application No. CA 3,028,509.

Randa, Z. et al., "Fast determination of gold in large mass samples of gold ores by photoexcitation reactions using 10 MeV bremsstrahlung", Journal of Radioanalytical and Nuclear Chemistry, Mar. 2007, pp. 603-606, vol. 271, No. 3.

* cited by examiner

ACCELERATOR SYSTEM FOR MINERAL COMPONENT ANALYSIS, SYSTEM AND METHOD FOR MINERAL COMPONENT ANALYSIS

CROSS-REFERENCE TO RELATED APPLICATIONS

The present application is based on and claims priority to Chinese Application No. 201711435413.2, filed on Dec. 26, 2017, entire contents of which is hereby incorporated by reference.

TECHNICAL FIELD

The present disclosure relates to radiation technology and, in particular, to an accelerator system and system and method for mineral component analysis.

BACKGROUND

One of the most concerned issues in current gold ore dressing and prospecting process is how to analyze a gold content in the mining area as quickly and efficiently as possible while ensuring accuracy. In the traditional atomic fluorescence spectrometry, a sample is required to be ground and dissolved, and then heated a specific high temperature for several hours with a variety of chemicals (or is processed by other operations) to obtain an analysis result for gold content. This process takes a long time, is complicated to operate, and requires to use chemicals such as strong acids. The present disclosure utilizes radiation technology to analyze mineral components and can effectively overcome the above problems.

SUMMARY

According to an aspect of the present disclosure, an accelerator system for mineral component analysis is provided, the accelerator system including: an electron gun for generating an electron beam; an accelerating tube for accelerating the electron beam emitted by the electron gun to a predetermined energy; a composite target for receiving the electron beam to generate a radioactive ray on the composite target; and a shielding mechanism for shielding the radioactive ray.

In an exemplary embodiment of the present disclosure, further comprising: a microwave system for providing a microwave electromagnetic field to the accelerating tube to accelerate the electron beam to the predetermined energy.

In an exemplary embodiment of the present disclosure, wherein the predetermined energy of the electron beam after acceleration of the accelerating tube is 8.5 MeV-14 MeV, and wherein an energy of the electron beam after acceleration of the accelerating tube is continuously adjustable.

In an exemplary embodiment of the present disclosure, wherein the radioactive ray produced by the composite target comprises X-ray.

In an exemplary embodiment of the present disclosure, the shielding mechanism comprises a first shielding layer and a second shielding layer; material of the first shielding layer is a lead material and a tungsten material, and material of the second shielding layer is a boron-containing polyethylene material.

According to an aspect of the present disclosure, a system for mineral component analysis, comprising: an accelerator system for mineral component analysis comprising: an electron gun for generating an electron beam; an accelerating tube for accelerating the electron beam emitted by the electron gun to a predetermined energy; a composite target for receiving the electron beam to generate a radioactive ray on the composite target; and a shielding mechanism for shielding the radioactive ray; a detector for receiving the radioactive ray and generating ray data for subsequent analysis; and a conveying device for moving a sample to be tested between a front end of the composite target and a detector.

In an exemplary embodiment of the present disclosure, further comprising: an overall compartment structure comprising a first compartment, a second compartment and a third compartment arranged side by side; the detector and the conveying device are located at the first compartment; the composite target, the electron gun, the accelerating tube and the shielding mechanism are located at the second compartment; and the microwave system is located at the third compartment.

In an exemplary embodiment of the present disclosure, further comprising a carrying device, wherein the accelerating tube is secured to the second compartment by the carrying device comprising a frame mechanism and a drawing mechanism.

In an exemplary embodiment of the present disclosure, wherein the accelerating tube is mounted to the frame mechanism; the drawing mechanism is connected with the frame mechanism and the frame mechanism is linearly moveable relative to the drawing mechanism.

In an exemplary embodiment of the present disclosure, the first compartment, the second compartment and the third compartment are respectively independent movable container compartment structures; and a connection manner between the first compartment, the second compartment and the third compartment comprises: positioning and mounting the first compartment and the second compartment by a sample conveying device; positioning and mounting the second compartment and the third compartment by a waveguide position in a microwave system.

According to an aspect of the present disclosure, a method of mineral composition analysis includes: generating a predetermined energy of radioactive ray by an accelerator; irradiating a reference substance and a sample containing a target element by the predetermined energy of radioactive ray; acquiring a first detection data from the sample and a second detection data from the reference substance by a detector; and determining a content of the target element in the sample by comparing the first detection data with the second detection data.

BRIEF DESCRIPTION OF THE DRAWINGS

The above and other objects, features and advantages of the present disclosure will become more apparent from the example embodiments of the present disclosure with reference to the accompanying drawings.

DETAILED DESCRIPTION

Example embodiments will now be described more fully with reference to the accompanying drawings.

Figure 1:
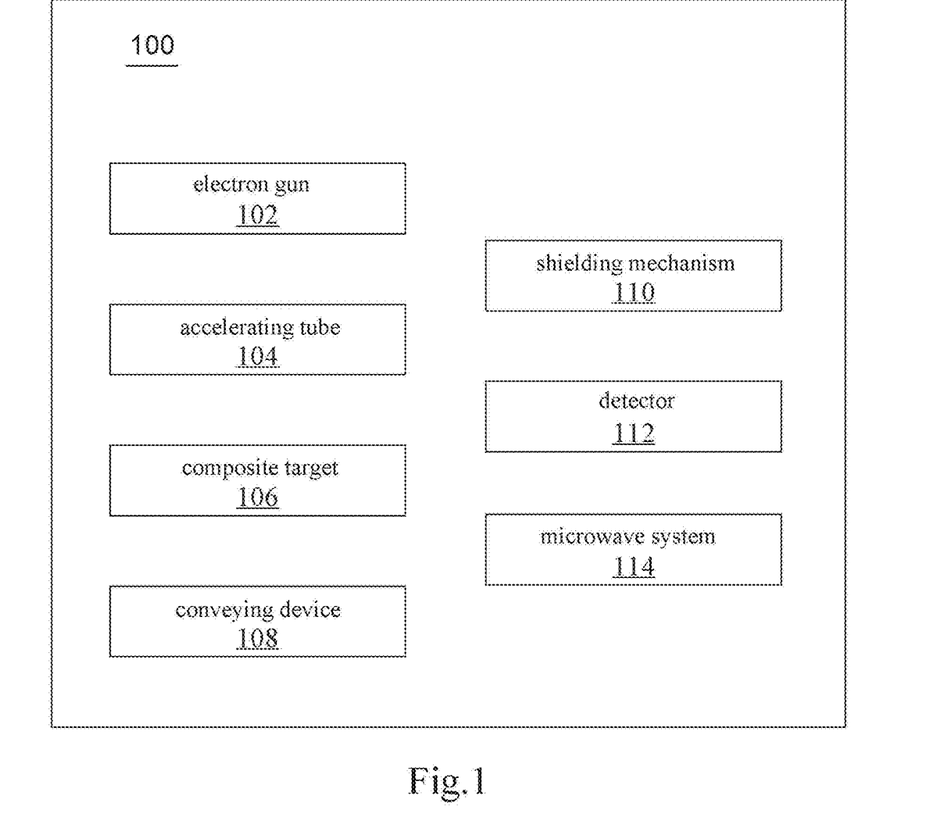
FIG. 1 is a system block diagram of an accelerator system for mineral component analysis, according to an exemplary embodiment.

FIG. 1 is a system block diagram of an accelerator system for mineral component analysis, according to an exemplary embodiment. The accelerator system 100 may include an electron gun 102, an accelerating tube 104, a composite target 106, a shielding mechanism 110, and a microwave system 114. According to an aspect of the present disclosure, a system for mineral component analysis comprises the above accelerator system for mineral component analysis, a detector 112 and conveying device 108.

The electron gun 102 is used to generate an electron beam. In the present application, the electron gun 102 may be, for example, a conventional diode gun, or may be, for example, a grid gun power supply.

In order to achieve a third-grade energy switchable requirement, the accelerator system 100 in the present application needs to control the beam load, so it is necessary to achieve an object of energy switching by changing an injection voltage and a gun emission current of the electron gun. According to working requirements of a grid-controlled electron gun, design specifications of a power supply of the grid-controlled gun may be adjusted.

The accelerating tube 104 is used to accelerate the electron beam emitted by the electron gun 102 to a predetermined energy. The accelerating tube 104 has an electronic input port and a microwave feed inlet. The electronic input port is coupled with an output end of the electron gun to receive the electron beam, and the microwave feed inlet is coupled with an output end of the microwave power source. The predetermined energy of the electron beam after accelerated by the accelerating tube 104 into which a microwave generated by the microwave power source is fed is 8.5 MeV-14 MeV, wherein the energy of the electron beam after accelerated by the accelerating tube 104 is continuously adjustable. In the present application, a magnetic coupling structure is used between tube cavities of the accelerating tube 104. Preferably, a design in which opposite sides are coupled has a smaller lateral dimension and a more compact structure. The double-cycle standing wave acceleration structure is used. Preferably, the overall length of the accelerating tube 104 is 1.2 m, and the tube body is water-cooled with a sleeve.

The composite target 106 is configured to generate radioactive ray on the composite target 106 after receiving bombardment of the electron beam. The radioactive ray generated by the composite target 106 includes X-ray. The scanning structure of the composite target 106 is divided into two sections, and a ceramic is added therebetween for isolation in order to facilitate acquisition of the target stream. To realize requirement for the same width of the electron beam under different energies, the current of the scanning magnet is controlled to adapt to deflection requirements with different energies.

In the present application, the composite target 106 may, for example, has a gold-copper composite target structure capable of producing a larger dose of X-ray. The composite target uses water-cooling method, specifically, forming three routes of water cooling by changing the composite target structure, to achieve sufficient cooling of the target area and to avoid damage to the target structure due to excessive temperature.

The conveying device 108 is configured to move the sample to be tested between the front end of the composite target and the detector.

The shielding mechanism 110 is used to shield the radioactive ray. The shielding mechanism 110 includes a first shielding layer 1101 and a second shielding layer 1102; wherein material of the first shielding layer 1101 is a lead material and a tungsten material, and material of the second shielding layer 1102 is a boron-containing polyethylene material. Due to high energy of the X-ray, the shielding system includes shielding protection for both X-ray and neutron radiation. With respect to the X-ray, shielding is performed with lead and tungsten, and neutron protection is provided to shield with boron-containing polyethylene. The first shielding layer 1101 includes an accelerating tube bracket fixing the accelerating tube, a transmission waveguide, a scanning box, the target and the scanning magnet together. Coupling waveguide from the accelerating tube 104 to the electron gun 102, a part in close contact with the accelerating tube 104 is primarily shielded and mounted in the machine head bracket. There is no primary shielding from the accelerating tube to the target and size of the bracket size is as small as possible. The bracket is fixed to the second shielding layer 1102 at the front end of the coupler, the accelerating tube bracket carries the primary shielding, and forms an integral shielding system after abutted against the second shielding layer 1102. The external environmental dose of the shielding is ensured to meet relevant local legal requirements.

The detector 112 is used to receive the radioactive ray and generate ray data for subsequent analysis.

The microwave system 114 is used to provide a microwave electromagnetic field for the accelerating tube to accelerate the electron beam to the predetermined energy. The microwave system 114 is a basic component of the electronic linear accelerator, including a high power microwave source and a microwave transmission system. The microwave power source is used to generate microwaves of different frequencies. Because the system requires higher dose output, a velocity modulated tube is used as the power source, and may obtain higher microwave input power. A low power microwave excitation source is provided as driving, and the microwave system 114 in the velocity modulated tube may, for example, be a high-power velocity modulated tube.

The waveguide transmission system 114 is composed of various passive microwave components, and its main function is to feed the power outputted by the microwave source into the accelerating tube to excite the electromagnetic field required for stimulating and accelerating the electron; and to provide a monitoring signal for the frequency and power of the system operation.

The accelerator system 100 further includes a control device (not shown) which is coupled to the microwave power source and the electron gun, and controls and the microwave power source to generate microwaves of different frequencies, so that the accelerating tube is switched between different resonant modes to produce an electron beam of corresponding energy.

The accelerator system for mineral component analysis according to the present disclosure is capable of providing an electron beam with a predetermined energy, a predetermined energy level, and a predetermined ray size, and achieves stable high-pressure out-beam, high repetition frequency long-term operation.

The design parameters of implementation of the accelerator system 100 for mineral component analysis of the present disclosure are as follows:

| Technical Indexes of Three-grade Energy Beam | | |
|---|---|---|
| Energy/MeV | Dose Rate/cGy/min@1 m | ray size/mm × mm |
| 8.5 | 16000 | 10 × 70 |
| 12 | 4000 | 10 × 70 |
| 14 | 2500 | 10 × 70 |

The energy index in the table is divided into three grades. The energy of 8.5 MeV can be used for identification of the gold element. The dose index of 16000 cGy/min@1 m can ensure the full activation of the sample in a short time, improve the working efficiency, and select the linear ray instead of traditional point source ray for the ray size, so that the sample can be fully illuminated to improve detection accuracy. The other two energy grades can be used for identification of non-precious metal elements such as copper, tantalum and lead.

Figure 2:
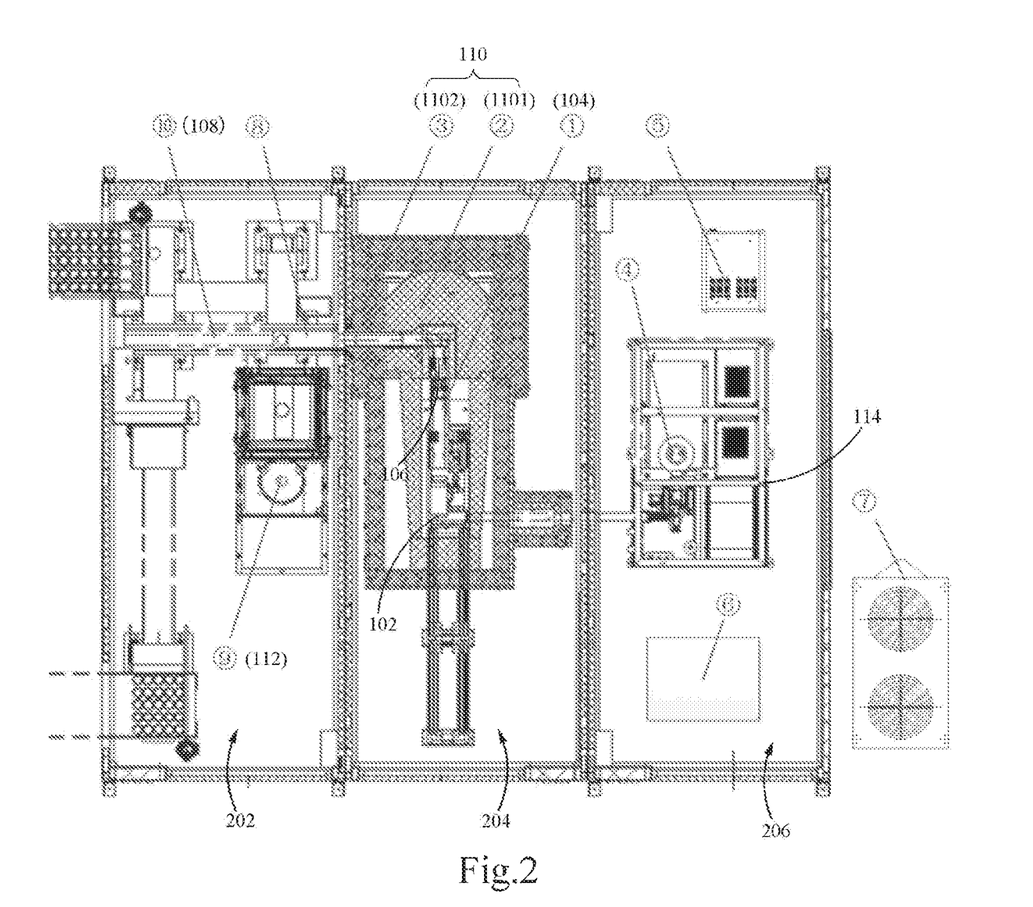
FIG. 2 is a block diagram of a compartment structure in an accelerator system for mineral component analysis, according to an exemplary embodiment.

FIG. 2 is a block diagram of a compartment structure of an accelerator system for mineral component analysis, according to an exemplary embodiment.

The overall compartment structure is distributed as shown in FIG. 2. Three container compartments are arranged side by side from left to right, which are a first compartment 202, a second compartment 204 and a third compartment 206, respectively. Preferably, the detector 112 and the conveying device 108 are located in the first compartment 202; the composite target 106, the electron gun 102, the accelerating tube 104 and the shielding mechanism 110 are located in the second compartment 204; and the microwave system 114 is located in the third compartment 206.

Figure 4:
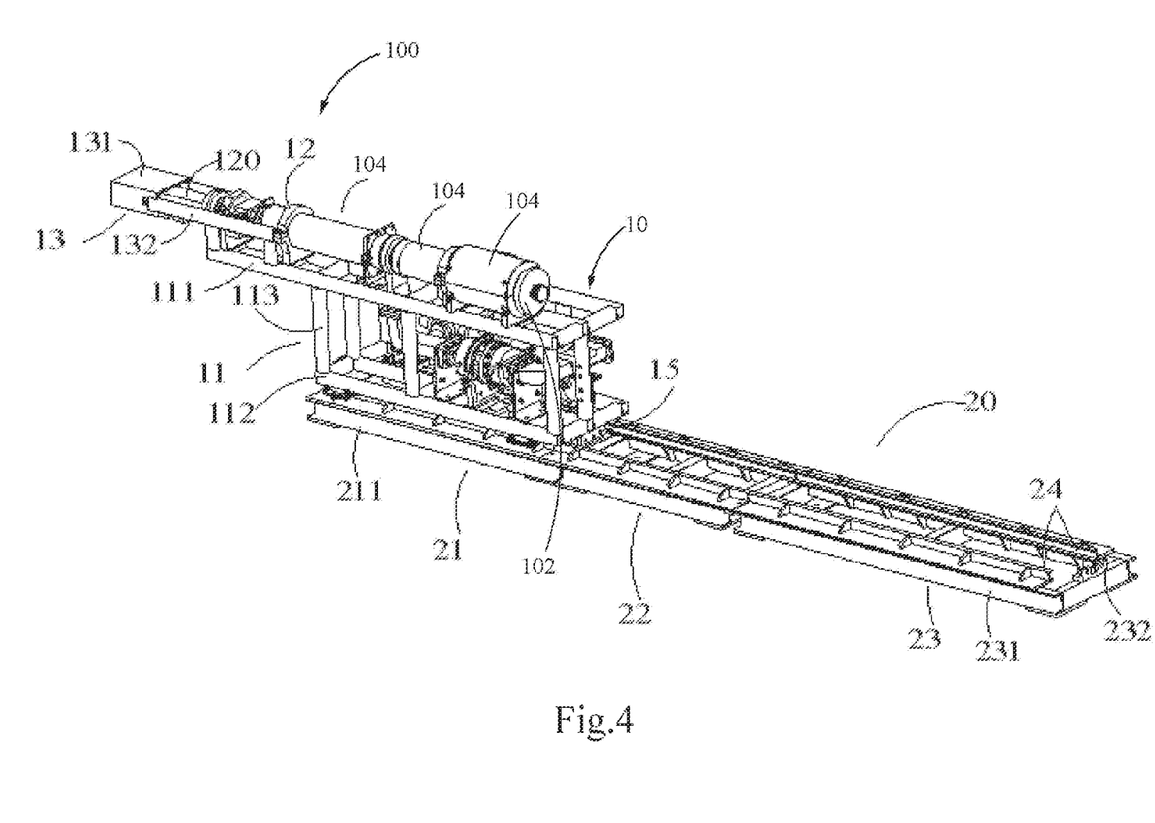
FIG. 4 is a perspective view of a drawing mechanism in an accelerator system for mineral component analysis, according to an exemplary embodiment.

The accelerating tube 104 is secured to the second compartment 204 by a carrying device, as shown in FIG. 4, which includes a frame mechanism 10 and a drawing mechanism 20. The frame mechanism 10 is used to install the accelerator system 100. The drawing mechanism 20 is connected with the frame mechanism 10 and the frame mechanism 10 is movable relative to the drawing mechanism 20.

The accelerating tube 104 is mounted to the frame mechanism 10; the drawing mechanism 20 is connected with the frame mechanism 10, and the frame mechanism 10 is linearly movable relative to the drawing mechanism 20.

The first compartment 202, the second compartment 204 and the third compartment 206 are respectively independent movable container compartment structures; and a connection mode between the first compartment 202, the second compartment 204 and the third compartment 206 includes: positioning and mounting the first compartment 202 and the second compartment 204 by the sample conveying device 108; positioning and mounting the second compartment 204 and the third compartment 206 by the waveguide position in the microwave system 114.

The second compartment 204 may be, for example, an accelerator head compartment. In FIG. 2, ① is an accelerating tube main body, and ② and ③ are primary shielding (also referred to herein as first shielding layer 1101) and secondary shielding (also referred to herein as second shielding layer 1102) structures, wherein the lateral passage is a conveying sample passage. In the figure, ④ is the velocity modulated tube, which is mounted within the microwave head frame, ⑤ is the solid state modulator, ⑥ is the water cooling set indoor unit, the above three subsystem components are mounted in the right-side compartment, and the outlet end of the velocity modulated tube is connected to the intermediate compartment of the accelerating tube through the waveguide part to achieve feed of microwave power. The leftmost compartment contains ⑧ conveying passage. In the figure, ⑨ is the location of the detector, which is convenient for the sample to be detected quickly after irradiation. In the figure, ⑩ is the automatic sample conveying device. On the right side of these three container compartments is the water cooling set outdoor unit ⑦.

In the prior art, the accelerator system is a non-movable system, and in general, the outer compartment of the accelerator system is a one-piece structure. According to the accelerator system for mineral component analysis of the present disclosure, various components inside the accelerator system are respectively located in different movable container compartments, and the respective compartments are positioned and mounted relative to each other by components inside the accelerator system, so that the accelerator system is easy to disassemble. Thus, the accelerator system can be disassembled on site at the mining area, in order to perform on-site measurement in the mining area, which is suitable for more scenes.

Figure 3:
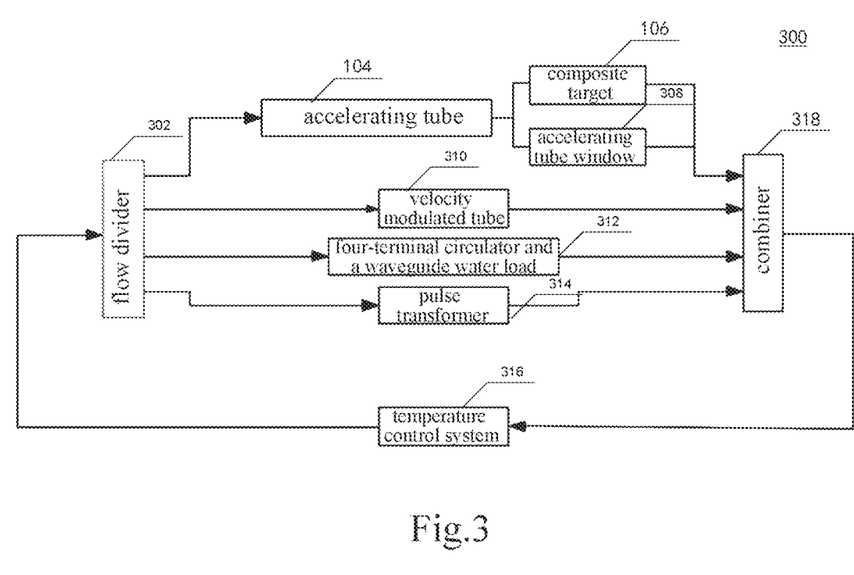
FIG. 3 is a schematic diagram of a water cooling system in an accelerator system for mineral component analysis, according to an exemplary embodiment.

FIG. 3 is a schematic diagram of a water cooling system of an accelerator system for mineral component analysis, according to an exemplary embodiment. The water cooling system 300 is connected as shown in FIG. 3. The water cooling system 300 includes a flow divider 302, a four-terminal circulator and a waveguide water load 312, a pulse transformer 314, a temperature control system 316, and a combiner 318.

Components of the accelerator system 10 that require cooling or constant temperature of the constant temperature water cooling system include an accelerating tube 104, a composite target 106, an accelerating tube window 308, a microwave window (not shown), a velocity modulated tube 310, and a four-terminal circulator 312, a three-terminal load (not shown), and a focus coil (not shown), and the like.

FIGS. 4-7 are schematic views of a drawing mechanism in an accelerator system for mineral component analysis, according to an exemplary embodiment.

In this embodiment, as shown in FIGS. 4 to 7, the carrying device includes a frame mechanism 10 and a drawing mechanism 20. The frame mechanism 10 is used to mount the accelerating tube 104. The drawing mechanism 20 is connected with the frame mechanism 10 and the frame mechanism 10 is movable relative to the drawing mechanism 20.

Figure 8:
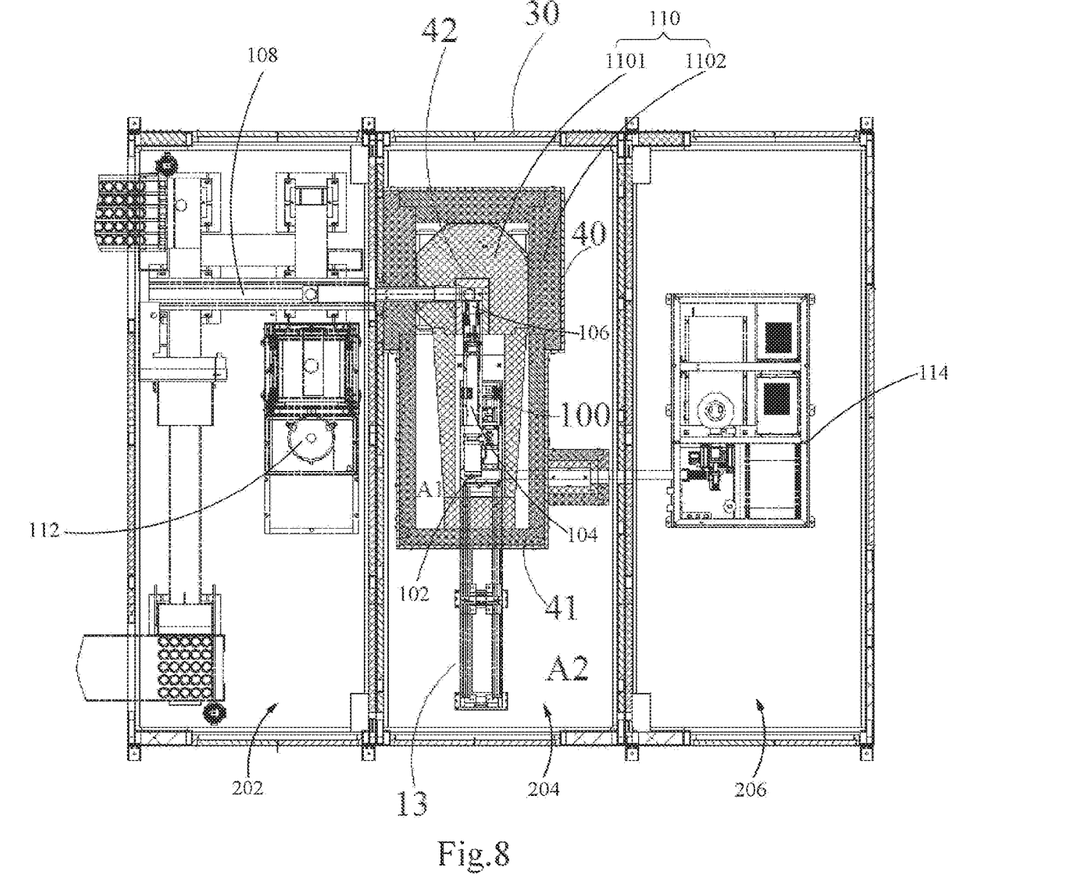
FIG. 8 is a top view of a compartment structure in an accelerator system for mineral component analysis, according to an exemplary embodiment.
Figure 9:
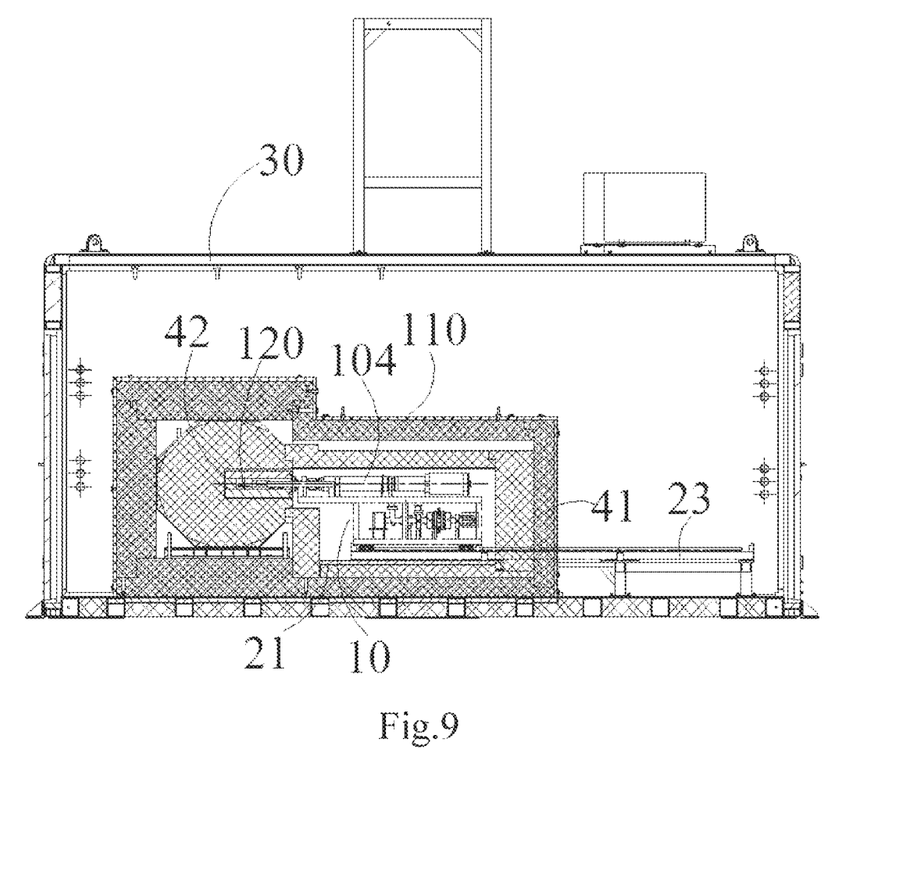
FIG. 9 is a cross-sectional view of a compartment structure in an accelerator system for mineral component analysis, according to an exemplary embodiment.

The carrying device may be applied to a cabin structure for an accelerator. As shown in FIGS. 8 and 9, the cabin structure for the accelerator may include a cabin 30, a shielding mechanism 110, and the above-mentioned drawer-type carrying device for the accelerator. The cabin 30 has a working area A1 and a maintenance area A2. The shielding mechanism 110 is disposed in the working area A1 and the shielding mechanism 110 has a side opening door 41 facing towards the maintenance area A2. The frame mechanism 10 is capable of drawn from the shielding mechanism 110 into the maintenance area A2 when the side opening door 41 is opened.

Therefore, when the accelerator system 100 needs to be adjusted or maintained, the frame mechanism 10 carrying the accelerator system 100 may be drawn, so that the accelerator system 100 located in the working area A1 is moved relative to the drawing mechanism 20 to the maintenance area A2, and adjustment and maintenance may be accomplished in the cabin 30.

Therefore, compared with the prior art, the present disclosure moves the accelerator system 100 in a drawing manner, which greatly reduces the operation difficulty and improving maintenance and adjustment efficiency of the high-power accelerator system 100. Moreover, by utilizing the drawer-type carrying device of the present disclosure, adjustment or maintenance can be accomplished inside the cabin structure for the accelerator. Therefore, it is not necessary to reserve a space volume outside the accelerator system 100 cabin 30, thereby improving utilization of the internal space of the cabin 30 and avoiding waste of the outer space of the cabin 30.

In this embodiment, as shown in FIGS. 1 and 2, the frame mechanism 10 may include a main frame 11 and at least one fixing and supporting seat 12. The fixing and supporting seat 12 is fixed to an upper side of the main frame 11, and the fixing and supporting seat 12 is used for supporting and fixing the accelerator system 100.

In this embodiment, the main frame 11 may include an upper support frame 111, a lower support frame 112, and a pillar 113 connected between the upper support frame 111 and the lower support frame 112. One end of the upper support frame 111 is longitudinally aligned with one end of the lower support frame 112, and the other end of the upper support frame 111 protrudes longitudinally at the other end of the lower support frame 112. The fixing and supporting seat 12 is fixed to the upper support frame 111.

In the present embodiment, the accelerator system 100 includes an acceleration tube 110 and a target guard assembly 120. One end of the target guard assembly 120 is connected to one end of the acceleration tube 110. The frame mechanism 10 may further include a shielding mechanism 13 detachably connected to the upper support frame 111 and protruding relative to the other end of the upper support frame 111. The shielding mechanism 13 is capable of covering the other end of the target guard assembly 120.

In this embodiment, the shielding mechanism 13 may include a cover body 131 and a connecting portion 132. The connecting portion 132 is protruded and fixed to the other end of the upper support frame 111, and the cover body 131 is detachably connected with the connecting portion 132. A material outside the cover body 131 may be stainless steel, and a material of an inner liner may be lead.

When the actual ejection is performed, the shielding mechanism 13 is removed and the target guard assembly 120 is exposed. During the maintenance process, the accelerator system 100 connects the shielding mechanism 13 to the upper support frame 111 to cover one end of the target guard assembly 120. Particularly, with respect to the accelerator system 100 that generates X-rays, the shielding mechanism 13 is provided to provide radiation guard shielding protection at the time of beam ejection, and isolation protection against the activated target after beam stop, thereby preventing maintenance personnel from being radiated.

In this embodiment, the drawing mechanism 20 may include a first rail 21, a second rail 22, and a third rail 23 that are continuously arranged in the longitudinal direction of the frame mechanism 10. At least a pair of rollers 14 are disposed below the frame mechanism 10, and the roller 14 is capable of rolling on the first rail 21, the second rail 22 and the third rail 23 to bring the frame mechanism 10 to move linearly with respect to the drawing mechanism 20 in the longitudinal direction.

The first rail 21 is disposed in the working area A1, the third rail 23 is disposed in the maintenance area A2, a part of the second rail 22 is located in the working area A1, and the other part of the second rail 22 is located in the maintenance area A2.

Figure 5:
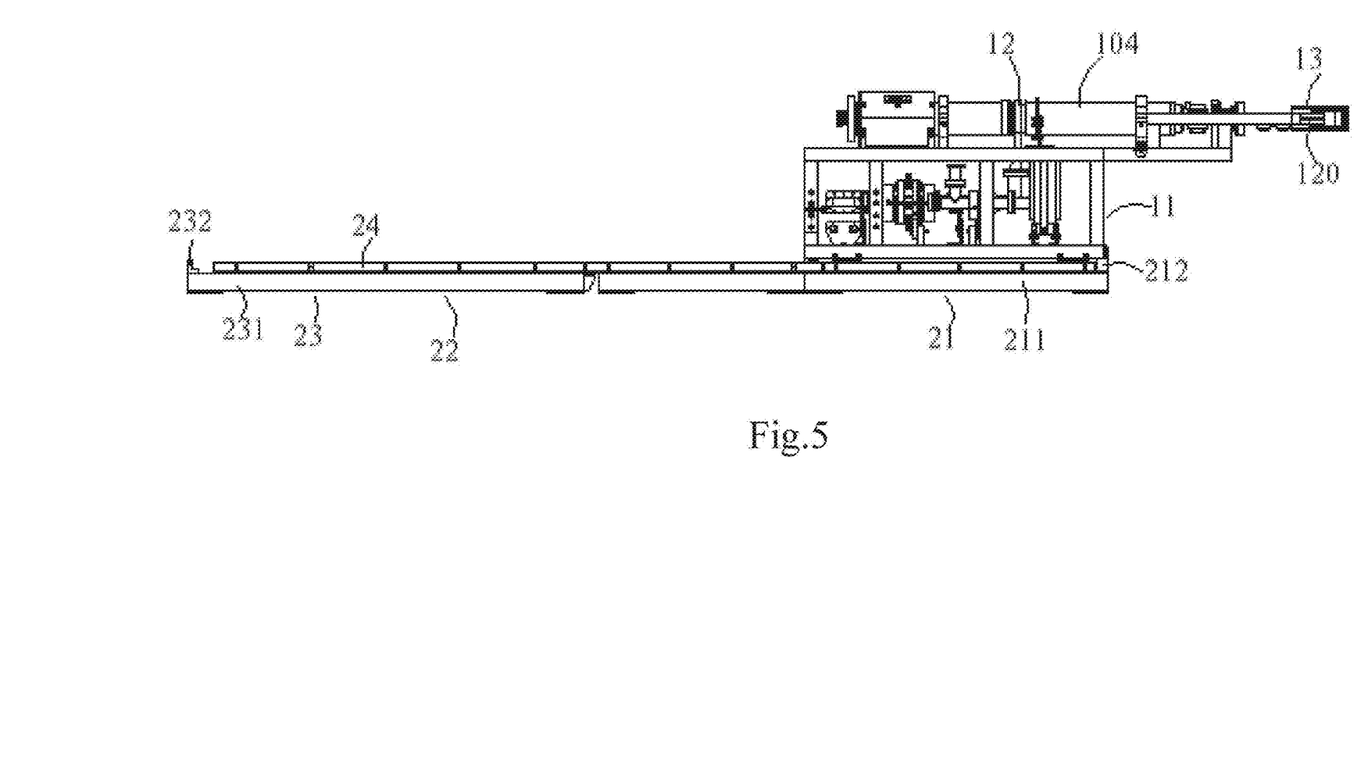
FIG. 5 is a front view of a drawing mechanism in an accelerator system for mineral component analysis, according to an exemplary embodiment.

As shown in FIG. 5, when the accelerator system 100 is in the operating state, the frame mechanism 10 is located in the shielding mechanism 110, a side opening door 41 of the shielding mechanism 110 is closed, and the second rail 22 is not installed.

When the accelerator system 100 needs to be maintained or adjusted, the side opening door 41 of the shielding mechanism 110 is opened and the second rail 22 is installed, so that the second rail 22 extends across the working area A1 and the maintenance area A2, and continuously arranged with the first rail 21 and the third rail 23 in a straight line to constitute a complete rail-type drawing mechanism 20. The frame mechanism 10 is movable along the first rail 21, the second rail 22, and the third rail 23 to enter the maintenance area A2.

In this embodiment, the corresponding rail may be disassembled or installed according to actual requirements, the installation of the rail is simple and fast, and it is not necessary to greatly modify the existing cabin structure for the accelerator. Therefore, the cabin structure for the accelerator of the embodiment has good operation and high applicability.

It should be understood that the number of rails is not limited thereto, and may be one, two or three or more, and may be adjusted according to actual conditions. Moreover, arrangement of the rails is not limited thereto, and may be in a curved arrangement. The manner of movement of the frame mechanism 10 is not limited to linear motion, and it may also be in a curved motion.

Figure 6:
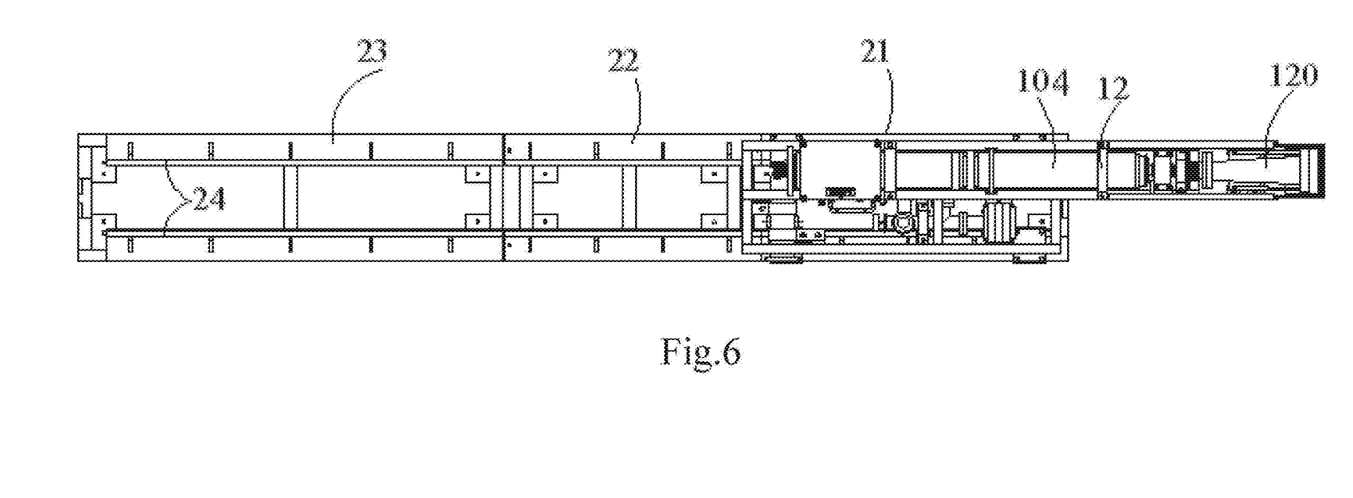
FIG. 6 is a top view of a drawing mechanism in an accelerator system for mineral component analysis, according to an exemplary embodiment.
Figure 7:
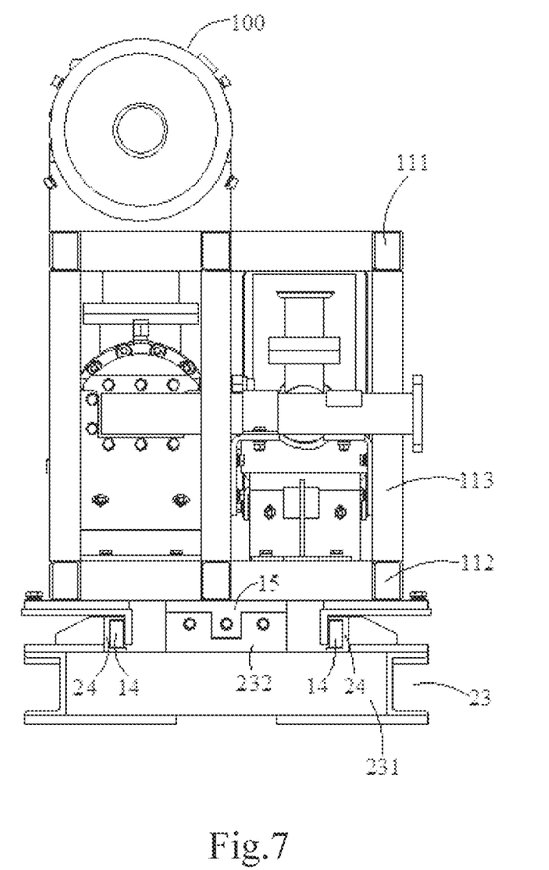
FIG. 7 is a side view of a drawing mechanism in an accelerator system for mineral component analysis, according to an exemplary embodiment.

In this embodiment, as shown in FIGS. 5 and 6, the shielding mechanism 110 may include a shielding cavity 42. The first rail 21 is disposed in alignment with the shielding cavity 42. The frame mechanism 10 is capable of entering the working area A1 along the first rail 21, and the target guard assembly 120 enters the shield cavity 42. Therefore, the rail is not only used for the drawing transmission, but also provides an alignment function for the installation of the acceleration tube 110 and the target guard assembly 120, thereby improving the installation efficiency and preventing the target from being damaged due to the misalignment of the target guard assembly 120.

In this embodiment, as shown in FIGS. 1 and 4, the first rail 21, the second rail 22 and the third rail 23 each include a pair of continuous and aligned guide grooves 24, and a height of the guide groove 24 is the same as a height of the roller 14. A spacing between the pair of guide grooves 24 is equal to a spacing between the pair of rollers 14. The pair of rollers 14 are capable of sliding in the guide groove 24 to bring the frame mechanism 10 to move longitudinally linearly with respect to the drawing mechanism 20, and the guide groove 24 can function to guide and limit the movement of the frame mechanism 10 so as to prevent the frame mechanism 10 from deviating from the rail.

In the present embodiment, as shown in FIGS. 1 and 4, the frame mechanism 10 may further include a fixing portion 15 located at both ends of the main frame 11 and protruding at the lower side of the main frame 11.

The first rail 21 further includes a first seat body 211. The guide groove 24 of the first rail 21 is fixed on the first seat body 211. One end of the first seat body 211 is provided with a first limit portion 212. When the frame mechanism 10 moves to a first position (the right end in FIG. 2), the fixing portion 15 at one end of the main frame 11 is abutted against by the first limit portion 212 and is capable of fixedly connecting with the first limit portion 212.

The third rail 23 further includes a third seat body 231. The guide groove 24 of the third rail 23 is fixed on the third seat body 231. One end of the third seat body 231 away from the first rail 21 is provided with a second limit portion 232. When the frame mechanism 10 moves to the second position (the left end in FIG. 2), the fixing portion 15 at the other end of the main frame 11 is abutted against by the second limit portion 232 and is capable of fixedly connecting with the second limit portion 232.

In this embodiment, fixing portions 15 at both ends of the frame mechanism 10 cooperate with limit portions at both ends of the drawing mechanism 20, and can define a maximum displacement amount of the frame mechanism 10 sliding on the drawing mechanism 20, and, in an extreme position, the fixing portion 15 is fixedly connected with the corresponding limit portion, so that the fastening of the frame mechanism 10 can be achieved to prevent the shaking thereof, and to improve accuracy and safety of the operation.

It should be understood that the form of the drawing mechanism 20 is not limited to the form of a rail, and any solution capable of achieving movement can be applied to the present disclosure, such as a conveyor belt, a hydraulic cylinder, or the like.

Specifically, the drawing mechanism may include a hydraulic cylinder, and a piston rod of the hydraulic cylinder is fixedly connected with the frame mechanism, and the piston rod can bring the frame mechanism to linearly move relative to a cylinder of the hydraulic cylinder during the expansion and contraction of the piston rod.

In summary, compared with the prior art, the present disclosure moves the accelerator in a drawing manner, which greatly reduces the operation difficulty and improving maintenance and adjustment efficiency of the high-power accelerator. Moreover, by utilizing the drawer-type carrying device of the present disclosure, adjustment or maintenance can be accomplished inside the cabin structure for the accelerator. Therefore, it is not necessary to reserve a space volume outside the accelerator cabin, thereby improving utilization of the internal space of the cabin and avoiding waste of the outer space of the cabin.

Figure 10:
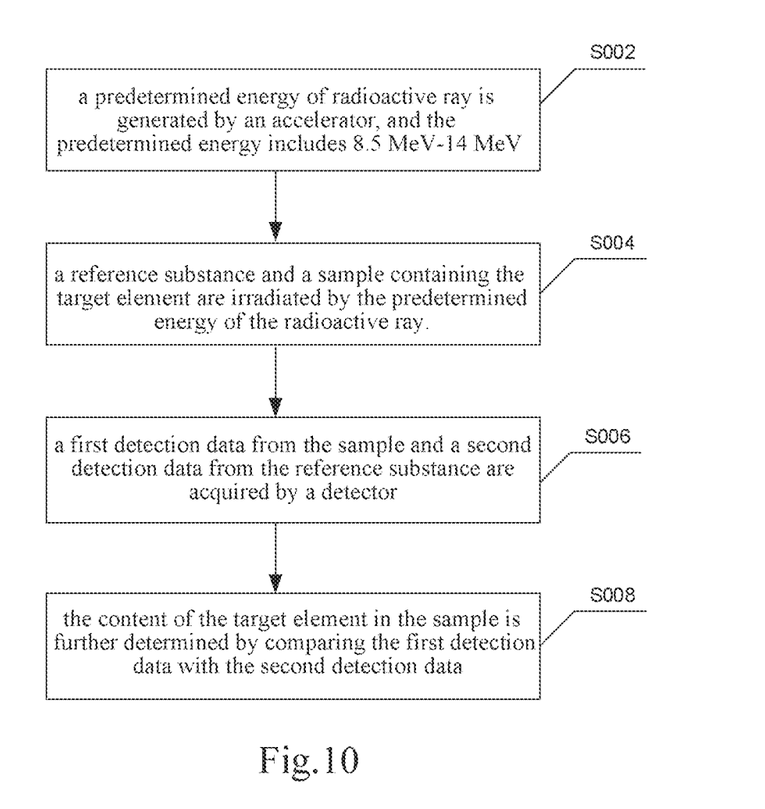
FIG. 10 is a flow chart of a method of mineral component analysis, according to another exemplary embodiment.

FIG. 10 is a flow chart of a method of mineral component analysis, according to another exemplary embodiment.

As shown in FIG. 10, in S002, a predetermined energy of radioactive ray is generated by an accelerator, and the predetermined energy includes 8.5 MeV-14 MeV.

In S004, a reference substance and a sample containing the target element are irradiated by the predetermined energy of the radioactive ray.

In S006, a first detection data from the sample and a second detection data from the reference substance are acquired by a detector.

In S008, the content of the target element in the sample is further determined by comparing the first detection data with the second detection data.

According to the method for mineral component analysis of the present disclosure, an analysis of the gold content of the sample to be tested can be performed quickly and accurately, with zero radio activity.

The exemplary embodiments of the present disclosure have been particularly shown and described above. It should be understood that the present disclosure is not limited to detailed structure, arrangement manner or implementing method described herein; rather, the present disclosure is intended to cover various modification and equivalences within spirit and scope of the appended claims.

What is claimed is:

1. An accelerator system for mineral component analysis, comprising:
   an electron gun for generating an electron beam;
   an accelerating tube for accelerating the electron beam emitted by the electron gun to a predetermined energy;
   a composite target for receiving the electron beam to generate a radioactive ray on the composite target; and
   a shielding mechanism for shielding the radioactive ray.

2. The accelerator system for mineral component analysis of claim 1 further comprising:
   a microwave system for providing a microwave electromagnetic field to the accelerating tube to accelerate the electron beam to the predetermined energy.

3. The accelerator system for mineral component analysis of claim 1, wherein the predetermined energy of the electron beam after acceleration of the accelerating tube is 8.5 MeV - 14 MeV, and wherein an energy of the electron beam after acceleration of the accelerating tube is continuously adjustable.

4. The accelerator system for mineral component analysis of claim 1, wherein the radioactive ray produced by the composite target comprises X-ray.

5. The accelerator system for mineral component analysis of claim 1, wherein
   the shielding mechanism comprises a first shielding layer and a second shielding layer;
   material of the first shielding layer is a lead material and a tungsten material, and material of the second shielding layer is a boron-containing polyethylene material.

6. A system for mineral component analysis, comprising:
   an accelerator system for mineral component analysis comprising:
      an electron gun for generating an electron beam;
      an accelerating tube for accelerating the electron beam emitted by the electron gun to a predetermined energy;
      a composite target for receiving the electron beam to generate a radioactive ray on the composite target; and
      a shielding mechanism for shielding the radioactive ray;
   a detector for receiving the radioactive ray and generating ray data for subsequent analysis; and
   a conveying device for moving a sample to be tested between a front end of the composite target and thea detector.

7. The system for mineral component analysis of claim 6, further comprising:

an overall compartment structure comprising a first compartment, a second compartment and a third compartment arranged side by side;

wherein the detector and the conveying device are located in the first compartment;

the composite target, the electron gun, the accelerating tube and the shielding mechanism are located in the second compartment; and a microwave system is located in the third compartment.

8. The system for mineral component analysis of claim 7, further comprising a carrying device, wherein the accelerating tube is secured to the second compartment by the carrying device comprising a frame mechanism and a drawing mechanism.

9. The system for mineral component analysis of claim 8, wherein the accelerating tube is mounted to the frame mechanism;

the drawing mechanism is connected with the frame mechanism and the frame mechanism is linearly moveable relative to the drawing mechanism.

10. The system for mineral component analysis of claim 7, wherein the first compartment, the second compartment and the third compartment are respectively independent movable container compartment structures; and a connection manner between the first compartment, the second compartment and the third compartment comprises:

positioning and mounting the first compartment and the second compartment by a sample conveying device;

positioning and mounting the second compartment and the third compartment by a waveguide position in the microwave system.

11. A method of mineral composition analysis, comprising:

generating an electron beam by an electron gun;

accelerating the electron beam emitted by the electron gun to a predetermined energy by an accelerating tube;

generating a predetermined energy of radioactive ray by a composite target after receiving bombardment of the electron beam with the predetermined energy from the accelerating tube;

shielding the radioactive ray by a shielding mechanism;

moving a sample to be tested between a front end of the composite target and a detector by a conveying device;

irradiating a reference substance and a sample containing a target element by the predetermined energy of the radioactive ray;

acquiring a first detection data from the sample and a second detection data from the reference substance by the detector; and determining a content of the target element in the sample by comparing the first detection data with the second detection data.

12. The method of mineral composition analysis according to claim 11, further comprises:

providing a microwave electromagnetic field to the accelerating tube to accelerate the electron beam to the predetermined energy.

13. The method of mineral composition analysis according to claim 11, wherein the predetermined energy of the electron beam after acceleration of the accelerating tube is 8.5 MeV - 14 MeV, and wherein an energy of the electron beam after acceleration of the accelerating tube is continuously adjustable.

14. The method of mineral composition analysis according to claim 11, wherein the radioactive ray produced by the composite target comprises X-ray.

15. The method of mineral composition analysis according to claim 11, wherein the method is performed by a system for mineral component analysis, the system further comprises:

an overall compartment structure comprising a first compartment, a second compartment and a third compartment arranged side by side; the detector and the conveying device are located in the first compartment, the composite target, the electron gun, the accelerating tube and the shielding mechanism are located in the second compartment; a microwave system is located in the third compartment; wherein the method further comprises:

positioning and mounting the first compartment and the second compartment by the conveying device;

positioning and mounting the second compartment and the third compartment by a waveguide position in the microwave system.

* * * * *